US007851482B2

(12) United States Patent
Dung et al.

(10) Patent No.: US 7,851,482 B2
(45) Date of Patent: Dec. 14, 2010

(54) METHOD FOR MAKING ANALGESICS

(75) Inventors: Jen-Sen Dung, Boothwyn, PA (US); Erno M. Keskeny, Wilmington, DE (US); James J. Mencel, North Wales, PA (US)

(73) Assignee: Johnson Matthey Public Limited Compnay, London (GB)

( * ) Notice: Subject to any disclaimer, the term of this patent is extended or adjusted under 35 U.S.C. 154(b) by 646 days.

(21) Appl. No.: 11/866,840

(22) Filed: Oct. 3, 2007

(65) Prior Publication Data

US 2008/0146601 A1 Jun. 19, 2008

(30) Foreign Application Priority Data

Dec. 14, 2006 (GB) .................................. 0624880.1

(51) Int. Cl.
*A61K 31/485* (2006.01)
*C07D 489/04* (2006.01)

(52) U.S. Cl. ............................. 514/282; 546/45; 546/44

(58) Field of Classification Search ................. 514/282; 546/45, 44
See application file for complete search history.

(56) References Cited

U.S. PATENT DOCUMENTS

| | | | |
|---|---|---|---|
| 3,332,950 A | 7/1967 | Blumberg et al. |
| 3,433,791 A | 3/1969 | Bentley |
| 3,812,132 A | 5/1974 | Grew et al. |
| 3,845,770 A | 11/1974 | Theeuwes et al. |
| 3,916,899 A | 11/1975 | Theeuwes et al. |
| 4,063,064 A | 12/1977 | Saunders et al. |
| 4,088,864 A | 5/1978 | Theeuwes et al. |
| 4,200,098 A | 4/1980 | Ayer et al. |
| 4,285,987 A | 8/1981 | Ayer et al. |
| 4,861,598 A | 8/1989 | Oshlack |
| 4,957,681 A | 9/1990 | Klimesch et al. |
| 5,071,985 A | 12/1991 | Andre et al. |
| 5,215,758 A | 6/1993 | Krishnamurthy |
| 5,273,760 A | 12/1993 | Oshlack et al. |
| 5,286,493 A | 2/1994 | Oshlack et al. |
| 5,324,351 A | 6/1994 | Oshlack et al. |
| 5,356,467 A | 10/1994 | Oshlack et al. |
| 5,472,712 A | 12/1995 | Oshlack et al. |
| 5,869,669 A | 2/1999 | Huang et al. |
| 5,922,876 A | 7/1999 | Huang et al. |
| 5,948,788 A | 9/1999 | Huang et al. |
| 5,952,495 A | 9/1999 | Huang et al. |
| 5,981,751 A | 11/1999 | Mudryk et al. |
| 6,008,354 A | 12/1999 | Huang et al. |
| 6,008,355 A | 12/1999 | Huang et al. |
| 6,013,796 A | 1/2000 | Huang et al. |
| 6,177,567 B1 | 1/2001 | Chiu et al. |
| 6,262,266 B1 | 7/2001 | Chiu et al. |
| 6,291,675 B1 | 9/2001 | Coop et al. |
| 6,365,742 B1 | 4/2002 | Mudryk et al. |
| 6,395,900 B1 | 5/2002 | Coop et al. |
| 6,403,798 B2 | 6/2002 | Chiu et al. |
| 6,723,894 B2 | 4/2004 | Fist et al. |
| 6,864,370 B1 | 3/2005 | Lin et al. |
| 6,949,645 B1 | 9/2005 | Francis |
| 7,071,336 B2 | 7/2006 | Francis et al. |
| 7,129,248 B2 | 10/2006 | Chapman et al. |
| 7,153,966 B2 | 12/2006 | Casner et al. |
| 2002/0045755 A1 | 4/2002 | Coop et al. |
| 2003/0129230 A1 | 7/2003 | Baichwal et al. |
| 2003/0129234 A1 | 7/2003 | Baichwal et al. |
| 2003/0157167 A1 | 8/2003 | Kao et al. |
| 2006/0009479 A1 | 1/2006 | Bailey et al. |
| 2006/0173029 A1 | 8/2006 | Chapman et al. |
| 2008/0045716 A1 | 2/2008 | Smith et al. |
| 2008/0125592 A1 | 5/2008 | Huang |
| 2008/0312442 A1 | 12/2008 | Buehler et al. |

FOREIGN PATENT DOCUMENTS

| | | |
|---|---|---|
| EP | 0 359 647 | 3/1990 |
| WO | WO 99/02529 | 1/1999 |
| WO | WO 01/29048 | 4/2001 |
| WO | WO 2005/028483 | 3/2005 |
| WO | WO 2007/103105 A2 * | 9/2007 |

OTHER PUBLICATIONS

Andrew Coop et al., "L-Selectride as a General Reagent for the O-Demethylation and N-Decarbomethoxylation of Opium Alkaloids and Derivatives," *J. Org. Chem.*, 1998, 63 (13), pp. 4392-4396.

Ulrich Weiss, Derivatives of Morphine. II. Demethylation of 14-hydroxycodeinone. 14-Hydroxymorphinone and 8,14-Dihydroxydihydromorphinone, *J. Org. Chem.*, 1957, 22 (11), pp. 1505-1508.

U.S. Appl. No. 12/446,171 which is a National Stage of PCT/US07/68009 to Bao-Shan Huang, filed May 2, 2007 and entitled "Process for Preparing Oxymorphone".

U.S. Appl. No. 12/446,172 which is the National Stage of PCT/US07/81513 to Bao-Shan Huang, filed Oct. 16, 2007 and entitled "Process for Preparing Oxymorphone, Naltrexone, and Buprenorphine".

Andre et al., "O-Demethylation of Opioid Derivatives with Methane Sulfonic Acid / Methionine: Application to the Synthesis of Naloxone and Analogues," *Synthetic Communications*, vol. 22, No. 16, pp. 2313-2327 (1992).

Hosztafi et al., "Reactions of Azodicarboxylic Esters with Amines," *Scientia Pharmaceutica*, vol. 55, pp. 61-75 (1987).

Marton et al., "Herstellung von 6, 14-Ethenomorphinan-Derivaten," *Monatshefte für Chemie*, vol. 125, pp. 1229-1239 (1994).

* cited by examiner

*Primary Examiner*—Charanjit S Aulakh
(74) *Attorney, Agent, or Firm*—RatnerPrestia

(57) ABSTRACT

Improved analgesic oxymorphone hydrochloride contains less than 10 ppm of alpha, beta unsaturated ketones and pharmaceutical preparations comprising such oxymorphone hydrochloride. The oxymorphone hydrochloride is produced by reducing a starting material oxymorphone hydrochloride using gaseous hydrogen and under specified acidity, solvent system and temperature conditions. A specific polymorph of oxymorphone hydrochloride may be obtained by hydration.

21 Claims, 1 Drawing Sheet

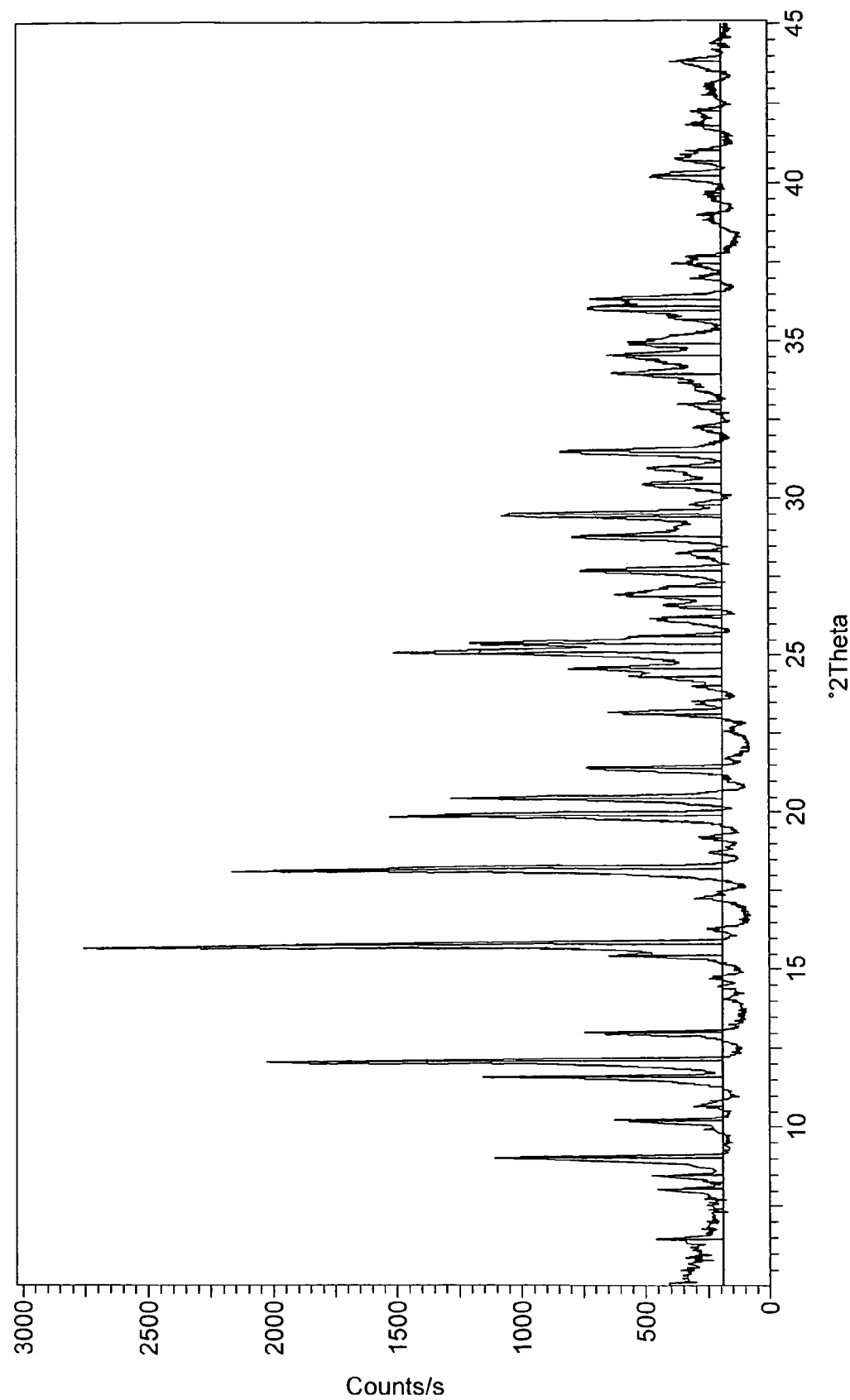

METHOD FOR MAKING ANALGESICS

FIELD OF THE INVENTION

This invention concerns an improved method for making analgesics, more especially for making the opiate oxymorphone as its hydrochloride.

BACKGROUND OF THE INVENTION

Oxymorphone, generally administered in the form of its hydrochloride salt, is a potent semi-synthetic opiate analgesic, for the relief of moderate to severe pain, and has been approved for use since 1959. It can be administered as an injectable solution, suppository, tablet or extended release tablet. It is desirable to develop high purity forms of oxymorphone and a method for its synthesis.

Several methods for synthesising oxymorphone from compounds isolated from the opium poppy or compounds derived therefrom are known, for example, starting from morphine, thebaine, or from oxycodone. There remains the need for methods which permit the formation of oxymorphone with low contamination of alpha, beta unsaturated ketones. The present invention provides an improved oxymorphone product and a method for producing such oxymorphone.

U.S. Pat. No. 7,129,248 claims a process for producing oxycodone hydrochloride with less than 25 ppm of 14-hydroxycodeinone, by hydrogenating oxycodone having greater than 100 ppm 14-hydroxycodeinone. The synthetic route to oxycodone taught in US'248 starts from thebaine and produces 14-hydroxycodeinone as an intermediate product and 8,14-dihydroxy-7,8-dihydrocodeinone as a by-product resulting from over-oxidation of thebaine. During conversion of oxycodone free base to the hydrogen chloride salt, the by-product may undergo acid-catalysed dehydration and be converted into 14-hydroxycodeinone. Thus the final oxycodone hydrogen chloride salt contains unreacted 14-hydroxycodeinone as well as 14-hydroxycodeinone derived from the by-product 8,14-dihydroxy-7,8-dihydrocodeinone. A hydrogenation step is claimed to reduce contents of 14-hydroxycodeinone from at least 100 ppm to less than 25 ppm.

SUMMARY OF THE INVENTION

The present invention provides an oxymorphone hydrochloride product containing less than 10 ppm of alpha, beta unsaturated ketones.

The invention also provides a method of purifying oxymorphone hydrochloride to yield an oxymorphone hydrochloride product containing less than 10 ppm of alpha, beta unsaturated ketones, which method comprises reducing a starting material oxymorphone hydrochloride in a strongly acid water and alcohol solvent, using gaseous hydrogen at a temperature in the range from 60 to 70° C. Reduction is suitably carried out for a period of at least 20 hours, but in another embodiment, reduction is carried out for 1 to 20 hours.

BRIEF DESCRIPTION OF THE DRAWINGS

The invention will be described below with reference to the drawing, in which:

FIG. 1 is the Powder X-Ray Diffraction pattern collected for a hydrated oxymorphone hydrochloride product made according to Example 3.2D.

DETAILED DESCRIPTION OF THE INVENTION

Preferably, the solvent is ethanol/water, although other water miscible alcohols, such as isopropanol and n-propanol, may be used. The reaction medium is very acidic, preferably by incorporating at least two equivalents of hydrochloric acid. A pH of less than 1 is desirable.

The reaction temperature is most preferably maintained at about 65° C. Hydrogen is conveniently supplied to the reaction vessel at 2.41 bar pressure.

The method of the invention has been able to reduce starting material oxymorphone hydrochloride having very high (of the order of 0.3 to 0.5%, or 3,000 to 5,000 ppm) content of alpha, beta unsaturated ketones to less than 10 ppm, and in many cases to undetectable levels (by HPLC).

The starting material oxymorphone hydrochloride may be an isolated or non-isolated material. Desirably, it has been obtained by the formation of the hydrogen chloride salt by heating oxymorphone free base in the presence of hydrochloric acid and an alcohol/water reaction medium. Suitable temperatures are 60-70° C. It can be seen that the reaction medium is ideal for the reduction of the method of the invention, so that it is generally not necessary to isolate the oxymorphone hydrochloride. However, the starting material oxymorphone hydrochloride may be isolated from the reaction medium or may be from another source.

The oxymorphone free base is itself preferably prepared by a reduction of 14-hydroxymorphinone. This may be carried out in a single- or two-stage process. The reduction is preferably carried out in acetic acid using gaseous hydrogen and a palladium on carbon catalyst. Preferred temperatures are of the order of 30° C. The base is precipitated by adding aqueous ammonia ($NH_4OH$).

This reduction may be in the presence of the reaction medium to which is added dichloromethane in methanol, Florasil and n-propanol.

The 14-hydroxymorphinone itself is most suitably prepared by hydroxylation of oripavine, using hydrogen peroxide in the presence of formic acid.

Oripavine is a known compound, which is extractable from poppy straw. The strain developed in Tasmania to be a high-Thebaine-yielding strain also produces higher than normal levels of oripavine.

The process of the invention is highly flexible, permitting many reaction steps to be carried out without isolation of intermediate products, whilst still retaining high (of the order of 50%) overall yields from oripavine, as well as remarkably high purity. Under favourable conditions, the presence of alpha, beta unsaturated ketones is undetectable by conventional means such as HPLC, but the skilled person can readily achieve less than 10 ppm contamination. The process of the invention has been successfully carried out at kilogram scale.

The oxymorphone hydrochloride having less than 10 ppm of alpha, beta unsaturated ketones can be incorporated into pharmaceutical dosage forms, e.g., by admixtures of the oxymorphone hydrochloride having less than 10 ppm of alpha, beta unsaturated ketones with conventional excipients, i.e., pharmaceutically acceptable organic or inorganic carrier substances. For oral formulations, the dosage forms can provide a sustained release of the active component. Suitable pharmaceutically acceptable carriers include but are not limited to, alcohols, gum arabic, vegetable oils, benzyl alcohols, polyethylene glycols, gelate, carbohydrates such as lactose, amylose or starch, magnesium stearate, talc, silicic acid, viscous paraffin, perfume oil, fatty acid monoglycerides and diglycerides, pentaerythritol fatty acid esters, hydroxy-methylcellulose, polyvinylpyrrolidone, etc. The pharmaceutical preparations can be sterilized and if desired mixed with auxiliary agents, e.g., lubricants, disintegrants, preservatives, stabilizers, wetting agents, emulsifiers, salts for influencing osmotic pressure buffers, colouring, flavouring and/or aromatic substances and the like. The compositions intended for oral use may be prepared according to any method known in the art and such compositions may contain one or more agents selected from the group consisting of inert, non-toxic pharmaceutically acceptable excipients that are suitable for the manufacture of tablets. Such excipients include, for example an inert diluent such as lactose; granulating and disintegrating agents such as cornstarch; binding agents such as starch; and lubricating agents such as magnesium stearate. The tablets may be uncoated or they may be coated by known techniques for elegance or to delay release of the active ingredients. Formulations for oral use may also be presented as hard gelatin capsules wherein the active ingredient is mixed with an inert diluent. The oral dosage forms of the present invention may be in the form of tablets (sustained release and/or immediate release), troches, lozenges, powders or granules, hard or soft capsules, microparticles (e.g., microcapsules, microspheres and the like), buccal tablets, solutions, suspensions, etc.

In certain embodiments, the present invention provides for a method of treating pain by administering to a human patient the dosage forms described herein.

When the dosage form is oral, the dosage form of the present invention contains from about 1 mg to about 40 mg of oxymorphone hydrochloride having less than 10 ppm of alpha, beta unsaturated ketones. Particularly preferred dosages are about 5 mg, about 10 mg, about 20 mg or about 40 mg however other dosages may be used as well. The oxymorphone hydrochloride having less than 10 ppm of alpha, beta unsaturated ketones can also be formulated with suitable pharmaceutically acceptable excipients to provide a sustained release of having less than 10 ppm of alpha, beta unsaturated ketones. Such formulations can be prepared in accordance with US 2003/129230 A1, US 2003/129234 A1 and US 2003/157167 A1.

The oxymorphone hydrochloride having less than 10 ppm of alpha, beta unsaturated ketones can be formulated as a sustained release oral formulation in any suitable tablet, coated tablet or multiparticulate formulation known to those skilled in the art. The sustained release dosage form may include a sustained release material that is incorporated into a matrix along with the oxymorphone salt thereof.

The sustained release dosage form may optionally comprise particles containing oxymorphone hydrochloride having less than 10 ppm of alpha, beta unsaturated ketones. In certain embodiments, the particles have a diameter from about 0.1 mm to about 2.5 mm, preferably from about 0.5 mm to about 2 mm. Preferably, the particles are film coated with a material that permits release of the active at a sustained rate in an aqueous medium. The film coat is chosen so as to achieve, in combination with the other stated properties, desired release properties. The sustained release coating formulations of the present invention should preferably be capable of producing a strong, continuous film that is smooth and elegant, capable of supporting pigments and other coating additives, non-toxic, inert, and tack-free.

Coated Beads

In certain embodiments of the present invention a hydrophobic material is used to coat inert pharmaceutical beads such as nu pariel 18/20 beads, and a plurality of the resultant solid sustained release beads may thereafter be placed in a gelatin capsule in an amount sufficient to provide an effective sustained release dose when ingested and contacted by an environmental fluid, e.g., gastric fluid or dissolution media.

The sustained release bead formulations of the present invention slowly release the active component of the present invention, e.g., when ingested and exposed to gastric fluids, and then to intestinal fluids. The sustained release profile of the formulations of the invention can be altered, for example, by varying the amount of overcoating with the hydrophobic material, altering the manner in which a plasticiser is added to the hydrophobic material, by varying the amount of plasticiser relative to hydrophobic material, by the inclusion of additional ingredients or excipients, by altering the method of manufacture, etc. The dissolution profile of the ultimate product may also be modified, for example, by increasing or decreasing the thickness of the retardant coating.

Spheroids or beads coated with the agent(s) of the present are prepared, e.g., by dissolving the agent(s) in water and then spraying the solution onto a substrate, for example, nu pariel 18/20 beads, using a Wuster insert. Optionally, additional ingredients are also added prior to coating the beads in order to assist the binding of the active to the beads, and/or to color the solution, etc. For example, a product that includes hydroxypropylmethylcellulose, etc with or without colorant (e.g., Opadry™, commercially available from Colorcon, Inc.) may be added to the solution and the solution mixed (e.g., for about 1 hour) prior to application of the same onto the beads. The resultant coated substrate, in these example beads, may then be optionally overcoated with a barrier agent, to separate the active component(s) from the hydrophobic sustained release coating. An example of a suitable barrier agent is one which comprises hydroxypropylmethylcellulose. However, any film-former known in the art may be used. It is preferred that the barrier agent does not affect the dissolution rate of the final product.

The beads may then be overcoated with an aqueous dispersion of the hydrophobic material. The aqueous dispersion of hydrophobic material preferably further includes an effective amount of plasticiser, e.g. triethyl citrate. Pre-formulated aqueous dispersions of ethylcellulose, such as Aquacoat™ or Surelease™, may be used. If Surelease™ is used, it is not necessary to separately add a plasticiser. Alternatively, pre-formulated aqueous dispersions of acrylic polymers such as Eudragit™ can be used.

The coating solutions of the present invention preferably contain, in addition to the film-former, plasticiser, and solvent system (i.e., water), a colorant to provide elegance and product distinction. Colour may be added to the solution of the therapeutically active agent instead, or in addition to the aqueous dispersion of hydrophobic material. For example, colour may be added to Aquacoat™ via the use of alcohol or propylene glycol based colour dispersions, milled aluminium lakes and opacifiers such as titanium dioxide by adding colour with shear to water soluble polymer solution and then using low shear to the plasticised Aquacoat™. Alternatively, any suitable method of providing colour to the formulations of the present invention may be used. Suitable ingredients for providing colour to the formulation when an aqueous dispersion of an acrylic polymer is used include titanium dioxide and colour pigments, such as iron oxide pigments. The incorporation of pigments, may, however, increase the retard effect of the coating.

Plasticised hydrophobic material may be applied onto the substrate comprising the agent(s) by spraying using any suitable spray equipment known in the art. In a preferred method, a Wurster fluidised-bed system is used in which an air jet, injected from underneath, fluidizes the core material and effects drying while the acrylic polymer coating is sprayed on. A sufficient amount of the hydrophobic material to obtain a predetermined sustained release of the agent(s) when the coated substrate is exposed to aqueous solutions, e.g. gastric fluid, may be applied. After coating with the hydrophobic material, a further overcoat of a film-former, such as Opadry™, is optionally applied to the beads. This overcoat is provided, if at all, in order to substantially reduce agglomeration of the beads.

The release of the agent(s) from the sustained release formulation of the present invention can be further influenced, i.e., adjusted to a desired rate, by the addition of one or more release-modifying agents, or by providing one or more passageways through the coating. The ratio of hydrophobic material to water soluble material is determined by, among other factors, the release rate required and the solubility characteristics of the materials selected.

The release-modifying agents, which function as pore-formers may be organic or inorganic, and include materials that can be dissolved, extracted or leached from the coating in an environment of use. The pore-formers may comprise one or more hydrophilic materials such as hydroxypropylmethylcellulose.

The sustained release coatings of the present invention can also include erosion-promoting agents such as starch and gums.

The sustained release coatings of the present invention can also include materials useful for making microporous lamina in the environment of use, such as polycarbonates comprised of linear polyesters of carbonic acid in which carbonate groups reoccur in the polymer chain.

The release-modifying agent may also comprise a semipermeable polymer.

In certain preferred embodiments, the release-modifying agent is selected from hydroxypropylmethylcellulose, lactose, metal stearates, and mixtures of any of the foregoing.

The sustained release coatings of the present invention may also include an exit means comprising at least one passageway, orifice, or the like. The passageway may be formed by such methods as those disclosed in U.S. Pat. No. 3,845,770, U.S. Pat. No. 3,916,899, U.S. Pat. No. 4,063,064 and U.S. Pat. No. 4,088,864.

Matrix Formulations

In other embodiments of the present invention, the sustained release formulation is achieved via a matrix optionally having a sustained release coating as set forth herein. The materials suitable for inclusion in a sustained release matrix may depend on the method used to form the matrix.

For example, a matrix in addition to the oxymorphone hydrochloride having less than 10 ppm of alpha, beta unsaturated ketones may include: hydrophilic and/or hydrophobic materials, such as gums, cellulose ethers, acrylic resins, protein derived materials. The list is not meant to be exclusive, any pharmaceutically acceptable hydrophobic material or hydrophilic material which is capable of imparting sustained release of the agent(s) and which melts (or softens to the extent necessary to be extruded) may be used in accordance with the present invention.

Digestible, long chain ($C_8$-$C_{50}$, especially $C_{12}$-$C_{40}$), substituted or unsubstituted hydrocarbons, such as fatty acids, fatty alcohols, glyceryl esters of fatty acids, mineral and vegetable oils and waxes, and stearyl alcohol; and polyalkylene glycols. Of these polymers, acrylic polymers, especially Eudragit™. RSPO—the cellulose ethers, especially hydroxyalkylcelluloses and carboxyalkylcelluloses, are preferred. The oral dosage form may contain between 1% and 80% (by weight) of at least one hydrophilic or hydrophobic material.

When the hydrophobic material is a hydrocarbon, the hydrocarbon preferably has a melting point of between 25° C. and 90° C. Of the long chain hydrocarbon materials, fatty (aliphatic) alcohols are preferred. The oral dosage form may contain up to 60% (by weight) of at least one digestible, long chain hydrocarbon.

Preferably, the oral dosage form contains up to 60% (by weight) of at least one polyalkylene glycol.

The hydrophobic material is preferably selected from the group consisting of alkylcelluloses, acrylic and methacrylic acid polymers and copolymers, shellac, zein, hydrogenated castor oil, hydrogenated vegetable oil, or mixtures thereof. In certain preferred embodiments of the present invention, the hydrophobic material is a pharmaceutically acceptable acrylic polymer, including but not limited to acrylic acid and methacrylic acid copolymers, methyl methacrylate, methyl methacrylate copolymers, ethoxyethyl methacrylates, cyanoethyl methacrylate, aminoalkyl methacrylate copolymer, poly(acrylic acid), poly(methacrylic acid), methacrylic acid alkylamine copolymer, poly(methyl methacrylate), poly(methacrylic acid) (anhydride), polymethacrylate, polyacrylamide, poly(methacrylic acid anhydride), and glycidyl methacrylate copolymers. In other embodiments, the hydrophobic material is selected from materials such as hydroxyalkylcelluloses such as hydroxypropylmethylcellulose and mixtures of the foregoing.

Preferred hydrophobic materials are water-insoluble with more or less pronounced hydrophilic and/or hydrophobic trends. Preferably, the hydrophobic materials useful in the invention have a melting point from about 25° C. to about 200° C., preferably from about 45° C. to about 90° C. Specifically, the hydrophobic material may comprise natural or synthetic waxes, fatty alcohols (such as lauryl, myristyl, stearyl, cetyl or preferably cetostearyl alcohol), fatty acids, including but not limited to fatty acid esters, fatty acid glycerides (mono-, di-, and tri-glycerides), hydrogenated fats, hydrocarbons, normal waxes, stearic aid, stearyl alcohol and hydrophobic and hydrophilic materials having hydrocarbon backbones. Suitable waxes include, for example, beeswax, glycowax, castor wax and carnauba wax. For the purposes of the present invention, a wax-like substance is defined as any material that is normally solid at room temperature and has a melting point of from about 25° C. to about 100° C.

Suitable hydrophobic materials which may be used in accordance with the present invention include digestible, long chain ($C_8$-$C_{50}$, especially $C_{12}$-$C_{40}$), substituted or unsubstituted hydrocarbons, such as fatty acids, fatty alcohols, glyceryl esters of fatty acids, mineral and vegetable oils and natural and synthetic waxes. Hydrocarbons having a melting point of between 25° C. and 90° C. are preferred. Of the long chain hydrocarbon materials, fatty (aliphatic) alcohols are preferred in certain embodiments. The oral dosage form may contain up to 60% (by weight) of at least one digestible, long chain hydrocarbon. Preferably, a combination of two or more hydrophobic materials are included in the matrix formulations. If an additional hydrophobic material is included, it is preferably selected from natural and synthetic waxes, fatty acids, fatty alcohols, and mixtures of the same. Examples include beeswax, carnauba wax, stearic acid and stearyl alcohol. This list is not meant to be exclusive.

One particular suitable matrix comprises at least one water soluble hydroxyalkyl cellulose, at least one $C_{12}$-$C_{36}$, preferably $C_{14}$-$C_{22}$, aliphatic alcohol and, optionally, at least one polyalkylene glycol. The at least one hydroxyalkyl cellulose is preferably a hydroxy ($C_1$ to $C_6$) alkyl cellulose, such as hydroxypropylcellulose, hydroxypropyl-methylcellulose and, especially, hydroxyethylcellulose. The amount of the at least one hydroxyalkyl cellulose in the present oral dosage form will be determined, inter alia, by the precise rate of oxymorphone hydrochloride release required. The at least one aliphatic alcohol may be, for example, lauryl alcohol, myristyl alcohol or stearyl alcohol. In particularly preferred embodiments of the present oral dosage form, however, the at least one aliphatic alcohol is cetyl alcohol or cetostearyl alcohol. The amount of the at least one aliphatic alcohol in the present oral dosage form will be determined, as above, by the precise rate of opioidoxycmorphone release required. It will also depend on whether at least one polyalkylene glycol is present in or absent from the oral dosage form. In the absence of at least one polyalkylene glycol, the oral dosage form preferably contains between 20% and 50% (by wt) of the at least one aliphatic alcohol. When at least one polyalkylene glycol is present in the oral dosage form, then the combined weight of the at least one aliphatic alcohol and the at least one polyalkylene glycol preferably constitutes between 20% and 50% (by wt) of the total dosage.

In one embodiment, the ratio of, e.g., the at least one hydroxyalkyl cellulose or acrylic resin to the at least one aliphatic alcohol/polyalkylene glycol determines, to a (w/w) of the at least one hydroxyalkyl cellulose to the at least one aliphatic alcohol/polyalkylene glycol of between 1:2 and 1:4 is preferred, with a ratio of between 1:3 and 1:4 being particularly preferred.

The at least one polyalkylene glycol may be, for example, polypropylene glycol or, preferably, polyethylene glycol. The number average molecular weight of the at least one polyalkylene glycol is preferably between 1,000 and 15,000 especially between 1,500 and 12,000.

Another suitable sustained release matrix would comprise an alkylcellulose (especially ethyl cellulose), a $C_{12}$ to $C_{36}$ aliphatic alcohol and, optionally, a polyalkylene glycol.

In another preferred embodiment, the matrix includes a pharmaceutically acceptable combination of at least two hydrophobic materials.

In addition to the above ingredients, a sustained release matrix may also contain suitable quantities of other materials, e.g. diluents, lubricants, binders, granulating aids, colorants, flavorants and glidants that are conventional in the pharmaceutical art.

Matrix—Particulates

In order to facilitate the preparation of a solid, sustained release, oral dosage form according to this invention, any method of preparing a matrix formulation known to those skilled in the art may be used. For example incorporation in the matrix may be effected, for example, by (a) forming granules comprising at least one water soluble hydroxyalkyl cellulose, and the oxymorphone hydrochloride having less than 10 ppm of alpha, beta unsaturated ketones; (b) mixing the hydroxyalkyl cellulose containing granules with at least one $C_{12}$ to $C_{36}$ aliphatic alcohol; and (c) optionally, compressing and shaping the granules. Preferably, the granules are formed by wet granulating the hydroxalkyl cellulose granules with water.

In yet other alternative embodiments, a spheronizing agent, together with the active component can be spheronized to form spheroids. Microcrystalline cellulose is a preferred spheronizing agent. A suitable microcrystalline cellulose is, for example, the material sold as Avicel PH 101 (Trade Mark, FMC Corporation). In such embodiments, in addition to the active ingredient and spheronizing agent, the spheroids may also contain a binder. Suitable binders, such as low viscosity, water soluble polymers, will be well known to those skilled in the pharmaceutical art. However, water soluble hydroxy lower alkyl cellulose, such as hydroxypropyl-cellulose, are preferred. Additionally (or alternatively) the spheroids may contain a water insoluble polymer, especially an acrylic polymer, an acrylic copolymer, such as a methacrylic acid-ethyl acrylate copolymer, or ethyl cellulose. In such embodiments, the sustained release coating will generally include a hydrophobic material such as (a) a wax, either alone or in admixture with a fatty alcohol; or (b) shellac or zein.

Melt Extrusion Matrix

Sustained release matrices can also be prepared via melt-granulation or melt-extrusion techniques. Generally, melt-granulation techniques involve melting a normally solid hydrophobic material, e.g. a wax, and incorporating a powdered drug therein. To obtain a sustained release dosage form, it may be necessary to incorporate an additional hydrophobic substance, e.g. ethylcellulose or a water-insoluble acrylic polymer, into the molten wax hydrophobic material. Examples of sustained release formulations prepared via melt-granulation techniques are found in U.S. Pat. No. 4,861,598.

The additional hydrophobic material may comprise one or more water-insoluble wax-like thermoplastic substances possibly mixed with one or more wax-like thermoplastic substances being less hydrophobic than said one or more water-insoluble wax-like substances. In order to achieve constant release, the individual wax-like substances in the formulation should be substantially non-degradable and insoluble in gastrointestinal fluids during the initial release phases. Useful water-insoluble wax-like substances may be those with a water-solubility that is lower than about 1:5,000 (w/w).

In addition to the above ingredients, a sustained release matrix may also contain suitable quantities of other materials, e.g., diluents, lubricants, binders, granulating aids, colourants, flavourants and glidants that are conventional in the pharmaceutical art. The quantities of these additional materials will be sufficient to provide the desired effect to the desired formulation.

In addition to the above ingredients, a sustained release matrix incorporating melt-extruded multiparticulates may also contain suitable quantities of other materials, e.g. diluents, lubricants, binders, granulating aids, colourants, flavourants and glidants that are conventional in the pharmaceutical art in amounts up to about 50% by weight of the particulate if desired.

Specific examples of pharmaceutically acceptable carriers and excipients that may be used to formulate oral dosage forms are described in the Handbook of Pharmaceutical Excipients, American Pharmaceutical Association (1986).

Melt Extrusion Multiparticulates

The preparation of a suitable melt-extruded matrix according to the present invention may, for example, include the steps of blending the oxymorphone hydrochloride having less than 10 ppm of alpha, beta unsaturated ketones together with at least one hydrophobic material and preferably the additional hydrophobic material to obtain a homogeneous mixture. The homogeneous mixture is then heated to a temperature sufficient to at least soften the mixture sufficiently to extrude the same. The resulting homogeneous mixture is then extruded to form strands. The extrudate is preferably cooled and cut into multiparticulates by any means known in the art. The strands are cooled and cut into multiparticulates. The multiparticulates are then divided into unit doses. The extrudate preferably has a diameter of from about 0.1 mm to about 5 mm and provides sustained release of the therapeutically active agent for a time period of from about 8 hours to about 24 hours.

An optional process for preparing the melt extrusions of the present invention includes directly metering into an extruder a hydrophobic material, the oxymorphone hydrochloride having less than 10 ppm of alpha, beta unsaturated ketones, and an optional binder; heating the homogenous mixture; extruding the homogenous mixture to thereby form strands; cooling the strands containing the homogeneous mixture; cutting the strands into particles having a size from about 0.1 mm to about 12 mm; and dividing said particles into unit doses. In this aspect of the invention, a relatively continuous manufacturing procedure is realized.

The diameter of the extruder aperture or exit port can also be adjusted to vary the thickness of the extruded strands. Furthermore, the exit part of the extruder need not be round; it can be oblong, rectangular, etc. The exiting strands can be reduced to particles using a hot wire cutter, guillotine, etc.

The melt extruded multiparticulate system can be, for example, in the form of granules, spheroids or pellets depending upon the extruder exit orifice. For the purposes of the present invention, the terms "melt-extruded multiparticulate(s)" and "melt-extruded multiparticulate system(s)" and "melt-extruded particles" shall refer to a plurality of units, preferably within a range of similar size and/or shape and containing one or more active agents and one or more excipients, preferably including a hydrophobic material as described herein. In this regard, the melt-extruded multiparticulates will be of a range of from about 0.1 mm to about 12 mm in length and have a diameter of from about 0.1 mm to about 5 mm. In addition, it is to be understood that the melt-extruded multiparticulates can be any geometrical shape within this size range. Alternatively, the extrudate may simply be cut into desired lengths and divided into unit doses of the therapeutically active agent without the need of a spheronization step.

In one preferred embodiment, oral dosage forms are prepared to include an effective amount of melt-extruded multiparticulates within a capsule. For example, a plurality of the melt-extruded multiparticulates may be placed in a gelatin capsule in an amount sufficient to provide an effective sustained release dose when ingested and contacted by gastric fluid.

In another preferred embodiment, a suitable amount of the multiparticulate extrudate is compressed into an oral tablet using conventional tabletting equipment using standard techniques. Techniques and compositions for making tablets (compressed and moulded), capsules (hard and soft gelatin) and pills are also described in Remington's Pharmaceutical Sciences, (Arthur Osol, editor), 1553-1593 (1980).

In yet another preferred embodiment, the extrudate can be shaped into tablets as set forth in U.S. Pat. No. 4,957,681, described in additional detail above.

Optionally, the sustained release melt-extruded multiparticulate systems or tablets can be coated, or the gelatin capsule containing the multiparticulates can be further coated, with a sustained release coating such as the sustained release coatings described above. Such coatings preferably include a sufficient amount of hydrophobic material to obtain a weight gain level from about 2% to about 30%, although the overcoat may be greater depending upon the desired release rate, among other things.

The melt-extruded unit dosage forms of the present invention may further include combinations of melt-extruded particles before being encapsulated. Furthermore, the unit dosage forms can also include an amount of an immediate release agent for prompt release. The immediate release agent may be incorporated, e.g., as separate pellets within a gelatin capsule, or may be coated on the surface of the multiparticulates after preparation of the dosage forms (e.g., sustained release coating or matrix-based). The unit dosage forms of the present invention may also contain a combination of sustained release beads and matrix multiparticulates to achieve a desired effect.

The sustained release formulations of the present invention preferably slowly release the agent(s), e.g. when ingested and exposed to gastric fluids, and then to intestinal fluids. The sustained release profile of the melt-extruded formulations of the invention can be altered, for example, by varying the amount of retardant, i.e., hydrophobic material, by varying the amount of plasticiser relative to hydrophobic material, by the inclusion of additional ingredients or excipients, by altering the method of manufacture, etc.

In other embodiments of the invention, the melt extruded material is prepared without the inclusion of the oxymorphone hydrochloride having less than 10 ppm of alpha, beta unsaturated ketones, which can be added thereafter to the extrudate. Such formulations typically will have the agents blended together with the extruded matrix material, and then the mixture would be tableted in order to provide a slow release formulation.

Coatings

The dosage forms of the present invention may optionally be coated with one or more materials suitable for the regulation of release or for the protection of the formulation. In one embodiment, coatings are provided to permit either pH-dependent or pH-independent release. A pH-dependent coating serves to release the active in desired areas of the gastrointestinal (GI) tract, e.g. the stomach or small intestine, such that an absorption profile is provided which is capable of providing at least about eight hours and preferably about twelve hours to up to about twenty-four hours of analgesia to a patient. When a pH-independent coating is desired, the coating is designed to achieve optimal release regardless of pH-changes in the environmental fluid, e.g., the GI tract. It is also possible to formulate compositions that release a portion of the dose in one desired area of the GI tract, e.g., the stomach, and release the remainder of the dose in another area of the GI tract, e.g., the small intestine.

Formulations according to the invention that utilize pH-dependent coatings to obtain formulations may also impart a repeat-action effect whereby unprotected drug is coated over the enteric coat and is released in the stomach, while the remainder, being protected by the enteric coating, is released further down the gastrointestinal tract. Coatings which are pH-dependent may be used in accordance with the present invention include shellac, cellulose acetate phthalate (CAP), polyvinyl acetate phthalate (PVAP), hydroxypropylmethylcellulose phthalate, and methacrylic acid ester copolymers, zein, and the like.

In certain preferred embodiments, the substrate (e.g., tablet core bead, matrix particle) containing the oxymorphone hydrochloride having less than 10 ppm of alpha, beta unsaturated ketones thereof is coated with a hydrophobic material selected from (i) an alkylcellulose; (ii) an acrylic polymer; or (iii) mixtures thereof. The coating may be applied in the form of an organic or aqueous solution or dispersion. The coating may be applied to obtain a weight gain from about 2% to about 25% of the substrate in order to obtain a desired sustained release profile. Coatings derived from aqueous dispersions are described in detail U.S. Pat. No. 5,273,760, U.S. Pat. No. 5,286,493, U.S. Pat. No. 5,324,351, U.S. Pat. No. 5,356,467, and U.S. Pat. No. 5,472,712.

Alkylcellulose Polymers

Cellulosic materials and polymers, including alkylcelluloses, provide hydrophobic materials well suited for coating the beads according to the invention. Simply by way of example, one preferred alkylcellulosic polymer is ethylcellulose, although the artisan will appreciate that other cellulose and/or alkylcellulose polymers may be readily employed, singly or in any combination, as all or part of a hydrophobic coating according to the invention.

Acrylic Polymers

In other preferred embodiments of the present invention, the hydrophobic material comprising the sustained release coating is a pharmaceutically acceptable acrylic polymer, including but not limited to acrylic acid and methacrylic acid copolymers, methyl methacrylate copolymers, ethoxyethyl methacrylates, cyanoethyl methacrylate, poly(acrylic acid), poly(methacrylic acid), methacrylic acid alkylamide copolymer, poly(methyl methacrylate), polymethacrylate, poly(methyl methacrylate) copolymer, polyacrylamide, aminoalkyl methacrylate copolymer, poly(methacrylic acid anhydride), and glycidyl methacrylate copolymers.

In certain preferred embodiments, the acrylic polymer is comprised of one or more ammonio methacrylate copolymers. Ammonio methacrylate copolymers are well known in the art, and are described as fully polymerised copolymers of acrylic and methacrylic acid esters with a low content of quaternary ammonium groups.

In order to obtain a desirable dissolution profile, it may be necessary to incorporate two or more ammonio methacrylate copolymers having differing physical properties, such as different molar ratios of the quaternary ammonium groups to the neutral (meth)acrylic esters.

Certain methacrylic acid ester-type polymers are useful for preparing pH-dependent coatings, which may be used in accordance with the present invention. For example, there are a family of copolymers synthesized from diethylaminoethyl methacrylate and other neutral methacrylic esters, also known as methacrylic acid copolymer or polymeric methacrylates, commercially available as Eudragit™ from Rohm Tech, Inc. There are several different types of Eudragit™, for example Eudragit™ E is an example of a methacrylic acid copolymer that swells and dissolves in acidic media. Eudragit™ L is a methacrylic acid copolymer which does not swell at about pH<5.7 and is soluble at about pH>6. Eudragit™ S does not swell at about pH<6.5 and is soluble at about pH>7. Eudragit™ RL and Eudragit™ RS are water swellable, and the amount of water absorbed by these polymers is pH-dependent, however, dosage forms coated with Eudragit™ RL and RS are pH-independent.

In certain preferred embodiments, the acrylic coating comprises a mixture of two acrylic resin lacquers commercially available from Rohm Pharma under the Tradenames Eudragit™ RL30D and Eudragit™ RS30D, respectively. Eudragit™ RL30D and Eudragit™ RS30D are copolymers of acrylic and methacrylic esters with a low content of quaternary ammonium groups, the molar ratio of ammonium groups to the remaining neutral (meth)acrylic esters being 1:20 in Eudragit™ RL30D and 1:40 in Eudragit™ RS30D. The mean molecular weight is about 150,000. The code designations RL (high permeability) and RS (low permeability) refer to the permeability properties of these agents. Eudragit™ RL/RS mixtures are insoluble in water and in digestive fluids. However, coatings formed from the same are swellable and permeable in aqueous solutions and digestive fluids.

The Eudragit™ RL/RS dispersions of the present invention may be mixed together in any desired ratio in order to ultimately obtain a sustained release formulation having a desirable dissolution profile. Desirable sustained release formulations may be obtained, for instance, from a retardant coating derived from 100% Eudragit™ RL, 50% Eudragit™ RL and 50% Eudragit™ RS, or 10% Eudragit™ RL and 90% Eudragit™ RS. Of course, one skilled in the art will recognize that other acrylic polymers may also be used, such as, for example, Eudragit™ L.

Plasticizers

In embodiments of the present invention where the coating comprises an aqueous dispersion of a hydrophobic material, the inclusion of an effective amount of a plasticiser in the aqueous dispersion of hydrophobic material will further improve the physical properties of the sustained release coating. For example, because ethyl-cellulose has a relatively high glass transition temperature and does not form flexible films under normal coating conditions, it is preferable to incorporate a plasticiser into an ethylcellulose coating containing sustained release coating before using the same as a coating material. Generally, the amount of plasticiser included in a coating solution is based on the concentration of the film-former, e.g., most often from about 1 wt % to about 50 wt % of the film-former. Concentration of the plasticiser, however, can only be properly determined after careful experimentation with the particular coating solution and method of application.

Examples of suitable plasticizers for ethylcellulose include water insoluble plasticizers such as dibutyl sebacate, diethyl phthalate, triethyl citrate, tributyl citrate, and triacetin, although it is possible that other water-insoluble plasticizers (such as acetylated monoglycerides, phthalate esters, castor oil, etc.) may be used. Triethyl citrate is an especially preferred plasticiser for the aqueous dispersions of ethyl cellulose of the present invention.

Examples of suitable plasticizers for the acrylic polymers of the present invention include, but are not limited to citric acid esters such as triethyl citrate, tributyl citrate, dibutyl phthalate, and possibly 1,2-propylene glycol. Other plasticizers that have proved to be suitable for enhancing the elasticity of the films formed from acrylic films such as Eudragit™ RL/RS lacquer solutions include polyethylene glycols, propylene glycol, diethyl phthalate, castor oil, and triacetin. Triethyl citrate is an especially preferred plasticiser for the aqueous dispersions of ethyl cellulose of the present invention.

The addition of a small amount of talc may also help reduce the tendency of the aqueous dispersion to stick during processing, and may act as a polishing agent.

Sustained Release Osmotic Dosage Form

Sustained release dosage forms according to the present invention may also be prepared as osmotic dosage formulations. The osmotic dosage forms preferably include a bilayer core comprising a drug layer (containing the oxymorphone hydrochloride having less than 10 ppm of alpha, beta unsaturated ketones) and a delivery or push layer, wherein the bilayer core is surrounded by a semipermeable wall and optionally having at least one passageway disposed therein.

The expression "passageway" as used for the purpose of this invention, includes aperture, orifice, bore, pore, porous element through which oxymorphone hydrochloride having less than 10 ppm of alpha, beta unsaturated ketones can be pumped, diffuse or migrate through a fibre, capillary tube, porous overlay, porous insert, microporous member, or porous composition. The passageway can also include a compound that erodes or is leached from the wall in the fluid environment of use to produce at least one passageway. Representative compounds for forming a passageway include erodible poly(glycolic) acid, or poly(lactic) acid in the wall; a gelatinous filament; a water-removable poly(vinyl alcohol); leachable compounds such as fluid-removable pore-forming polysaccharides, acids, salts or oxides. A passageway can be formed by leaching a compound from the wall, such as sorbitol, sucrose, lactose, maltose, or fructose, to form a sustained-release dimensional pore-passageway. The dosage form can be manufactured with one or more passageways in spaced-apart relation on one or more surfaces of the dosage form. A passageway and equipment for forming a passageway are disclosed in U.S. Pat. No. 3,845,770, U.S. Pat. No. 3,916,899, U.S. Pat. No. 4,063,064 and U.S. Pat. No. 4,088,864. Passageways comprising sustained-release dimensions sized, shaped and adapted as a releasing-pore formed by aqueous leaching to provide a releasing-pore of a sustained-release rate are disclosed in U.S. Pat. No. 4,200,098 and U.S. Pat. No. 4,285,987.

In certain embodiments the drug layer may also comprise at least one polymer hydrogel. The polymer hydrogel may have an average molecular weight of between about 500 and about 6,000,000. Examples of polymer hydrogels include but are not limited to a maltodextrin polymer comprising the formula $(C_6H_{12}O_5)_nH_2O$, wherein n is 3 to 7,500, and the maltodextrin polymer comprises a 500 to 1,250,000 number-average molecular weight; a poly(alkylene oxide) represented by, e.g., a poly(ethylene oxide) and a poly(propylene oxide) having a 50,000 to 750,000 weight-average molecular weight, and more specifically represented by a poly(ethylene oxide) of at least one of 100,000, 200,000, 300,000 or 400,000 weight-average molecular weights; an alkali carboxyalkylcellulose, wherein the alkali is sodium or potassium, the alkyl is methyl, ethyl, propyl, or butyl of 10,000 to 175,000 weight-average molecular weight; and a copolymer of ethylene-acrylic acid, including methacrylic and ethacrylic acid of 10,000 to 500,000 number-average molecular weight.

In certain embodiments of the present invention, the delivery or push layer comprises an osmopolymer. Examples of an osmopolymer include but are not limited to a member selected from the group consisting of a polyalkylene oxide and a carboxyalkylcellulose. The polyalkylene oxide possesses a 1,000,000 to 10,000,000 weight-average molecular weight. The polyalkylene oxide may be a member selected from the group consisting of polymethylene oxide, polyethylene oxide, polypropylene oxide, polyethylene oxide having a 1,000,000 average molecular weight, polyethylene oxide comprising a 5,000,000 average molecular weight, polyethylene oxide comprising a 7,000,000 average molecular weight, cross-linked polymethylene oxide possessing a 1,000,000 average molecular weight, and polypropylene oxide of 1,200,000 average molecular weight. Typical osmopolymer carboxyalkylcellulose comprises a member selected from the group consisting of alkali carboxyalkylcellulose, sodium carboxymethylcellulose, potassium carboxymethylcellulose, sodium carboxyethylcellulose, lithium carboxymethylcellulose, sodium carboxyethyl-cellulose, carboxyalkylhydroxyalkylcellulose, carboxymethylhydroxyethyl cellulose, carboxyethylhydroxyethylcellulose and carboxymethylhydroxypropylcellulose. The osmopolymers used for the displacement layer exhibit an osmotic pressure gradient across the semipermeable wall. The osmopolymers imbibe fluid into dosage form, thereby swelling and expanding as an osmotic hydrogel (also known as an osmogel), whereby they push the oxymorphone hydrochloride having less than 10 ppm of alpha, beta unsaturated ketones thereof from the osmotic dosage form.

The push layer may also include one or more osmotically effective compounds also known as osmagents and as osmotically effective solutes. They imbibe an environmental fluid, for example, from the gastrointestinal tract, into dosage form and contribute to the delivery kinetics of the displacement layer. Examples of osmotically active compounds comprise a member selected from the group consisting of osmotic salts and osmotic carbohydrates. Examples of specific osmagents include but are not limited to sodium chloride, potassium chloride, magnesium sulphate, lithium phosphate, lithium chloride, sodium phosphate, potassium sulphate, sodium sulphate, potassium phosphate, glucose, fructose and maltose.

The push layer may optionally include a hydroxypropylalkylcellulose possessing a 9,000 to 450,000 number-average molecular weight. The hydroxypropylalkyl-cellulose is represented by a member selected from the group consisting of hydroxypropylmethylcellulose, hydroxypropylethylcellulose, hydroxypropylisopropyl cellulose, hydroxypropylbutylcellulose, and hydroxypropylpentylcellulose.

The push layer optionally may comprise a non-toxic colorant or dye. Examples of colourants or dyes include but are not limited to Food and Drug Administration Colourants (FD&C), such as FD&C No. 1 blue dye, FD&C No. 4 red dye, red ferric oxide, yellow ferric oxide, titanium dioxide, carbon black, and indigo.

The push layer may also optionally comprise an antioxidant to inhibit the oxidation of ingredients. Some examples of antioxidants include but are not limited to a member selected from the group consisting of ascorbic acid, ascorbyl palmitate, butylated hydroxyanisole, a mixture of 2 and 3 tertiary-butyl-4-hydroxyanisole, butylated hydroxytoluene, sodium isoascorbate, dihydroguaretic acid, potassium sorbate, sodium bisulfate, sodium metabisulfate, sorbic acid, potassium ascorbate, vitamin E, 4-chloro-2,6-ditertiary butylphenol, alphatocopherol, and propylgallate.

In certain alternative embodiments, the dosage form comprises a homogenous core comprising oxymorphone hydrochloride having less than 10 ppm of alpha, beta unsaturated ketones, a pharmaceutically acceptable polymer (e.g., polyethylene oxide), optionally a disintegrant (e.g., polyvinylpyrrolidone), optionally an absorption enhancer (e.g., a fatty acid, a surfactant, a chelating agent, a bile salt, etc). The homogenous core is surrounded by a semipermeable wall having a passageway (as defined above) for the release of the oxymorphone hydrochloride having less than 10 ppm of alpha, beta unsaturated ketones.

In certain embodiments, the semipermeable wall comprises a member selected from the group consisting of a cellulose ester polymer, a cellulose ether polymer and a cellulose ester-ether polymer. Representative wall polymers comprise a member selected from the group consisting of cellulose acylate, cellulose diacylate, cellulose triacylate, cellulose acetate, cellulose diacetate, cellulose triacetate, mono-, di- and tricellulose alkenylates, and mono-, di- and tricellulose alkinylates. The poly(cellulose) used for the present invention comprises a number-average molecular weight of 20,000 to 7,500,000.

Additional semipermeable polymers for the purpose of this invention comprise acetaldehyde dimethycellulose acetate, cellulose acetate ethylcarbamate, cellulose acetate methylcarbamate, cellulose diacetate, propylcarbamate, cellulose acetate diethylaminoacetate; semipermeable polyamide; semipermeable polyurethane; semipermeable sulfonated polystyrene; semipermeable cross-linked polymer formed by the coprecipitation of a polyanion and a polycation, semipermeable crosslinked polystyrenes, semipermeable crosslinked poly(sodium styrene sulfonate), semipermeable crosslinked poly(vinylbenzyltrimethyl ammonium chloride) and semipermeable polymers possessing a fluid permeability of $2.5 \times 10^{-8}$ to $2.5 \times 10^{-2}$ ($cm^2$/hr atm) expressed per atmosphere of hydrostatic or osmotic pressure difference across the semipermeable wall. Other polymers useful in the present invention are known in the art including those in Handbook of Common Polymers, Scott, J. R. and W. J. Roff, 1971, CRC Press, Cleveland, Ohio.

In certain embodiments, preferably the semipermeable wall is nontoxic, inert, and it maintains its physical and chemical integrity during the dispensing life of the drug. In certain embodiments, the dosage form comprises a binder. An example of a binder includes, but is not limited to a therapeutically acceptable vinyl polymer having a 5,000 to 350,000 viscosity-average molecular weight, represented by a member selected from the group consisting of poly-n-vinylamide, poly-n-vinylacetamide, poly(vinyl pyrrolidone), also known as poly-n-vinylpyrrolidone, poly-n-vinylcaprolactone, poly-n-vinyl-5-methyl-2-pyrrolidone, and poly-n-vinyl-pyrrolidone copolymers with a member selected from the group consisting of vinyl acetate, vinyl alcohol, vinyl chloride, vinyl fluoride, vinyl butyrate, vinyl laureate, and vinyl stearate. Other binders include for example, acacia, starch, gelatin, and hydroxypropylalkylcellulose of 9,200 to 250,000 average molecular weight.

In certain embodiments, the dosage form comprises a lubricant, which may be used during the manufacture of the dosage form to prevent sticking to die wall or punch faces. Examples of lubricants include but are not limited to magnesium stearate, sodium stearate, stearic acid, calcium stearate, magnesium oleate, oleic acid, potassium oleate, caprylic acid, sodium stearyl fumarate, and magnesium palmitate.

In certain preferred embodiments, the present invention includes a therapeutic composition comprising an amount of oxymorphone hydrochloride having less than 10 ppm of alpha, beta unsaturated ketones equivalent to 10 to 40 mg oxymorphone hydrochloride, 25 mg to 500 mg of poly(alkylene oxide) having a 150,000 to 500,000 average molecular weight, 1 mg to 50 mg of polyvinylpyrrolidone having a 40,000 average molecular weight, and 0 mg to about 7.5 mg of a lubricant.

Suppositories

The sustained release formulations of the present invention may be formulated as a pharmaceutical suppository for rectal administration comprising a suitable suppository base, and oxymorphone hydrochloride having less than 10 ppm of alpha, beta unsaturated ketones. Preparation of sustained release suppository formulations is described in, e.g., U.S. Pat. No. 5,215,758.

Prior to absorption, the drug must be in solution. In the case of suppositories, solution must be preceded by dissolution of the suppository base, or the melting of the base and subsequent partition of the drug from the suppository base into the rectal fluid. The absorption of the drug into the body may be altered by the suppository base. Thus, the particular suppository base to be used in conjunction with a particular drug must be chosen giving consideration to the physical properties of the drug. For example, lipid-soluble drugs will not partition readily into the rectal fluid, but drugs that are only slightly soluble in the lipid base will partition readily into the rectal fluid.

Among the different factors affecting the dissolution time (or release rate) of the drugs are the surface area of the drug substance presented to the dissolution solvent medium, the pH of the solution, the solubility of the substance in the specific solvent medium, and the driving forces of the saturation concentration of dissolved materials in the solvent medium. Generally, factors affecting the absorption of drugs from suppositories administered rectally include suppository vehicle, absorption site pH, drug pKa, degree of ionisation, and lipid solubility.

The suppository base chosen should be compatible with the active of the present invention. Further, the suppository base is preferably non-toxic and non-irritating to mucous membranes, melts or dissolves in rectal fluids, and is stable during storage.

In certain preferred embodiments of the present invention for both water-soluble and water-insoluble drugs, the suppository base comprises a fatty acid wax selected from the group consisting of mono-, di- and triglycerides of saturated, natural fatty acids of the chain length $C_{12}$ to $C_{18}$.

In preparing the suppositories of the present invention other excipients may be used. For example, a wax may be used to form the proper shape for administration via the rectal route. This system can also be used without wax, but with the addition of diluent filled in a gelatin capsule for both rectal and oral administration.

Examples of suitable commercially available mono-, di- and triglycerides include saturated natural fatty acids of the 12-18 carbon atom chain sold under the trade name Novata™ (types AB, AB, B, BC, BD, BBC, E, BCF, C, D and 299), manufactured by Henkel, and Witepsol™ (types H5, H12, H15, H175, H185, H19, H32, H35, H39, H42, W25, W31, W35, W45, S55, S58, E75, E76 and E85), manufactured by Dynamit Nobel.

Other pharmaceutically acceptable suppository bases may be substituted in whole or in part for the above-mentioned mono-, di- and triglycerides. The amount of base in the suppository is determined by the size (i.e. actual weight) of the dosage form, the amount of base (e.g., alginate) and drug used. Generally, the amount of suppository base is from about 20% to about 90% by weight of the total weight of the suppository. Preferably, the amount of suppository base in the suppository is from about 65% to about 80%, by weight of the total weight of the suppository.

Additional Embodiments

The oxymorphone hydrochloride having less than 10 ppm of alpha, beta unsaturated ketones may be used as a substitute for the oxymorphone hydrochloride in any existing commercial product such as, e.g., Opana™, Opana ER™ and Numorphan™. Such formulations are listed in the FDA Orange Book.

EXAMPLES

The invention will now be illustrated by the following examples, showing the synthesis of the high purity oxymorphone, starting from oripavine.

FIG. 1 is the Powder X-Ray Diffraction pattern collected for a hydrated oxymorphone hydrochloride product made according to Example 3.2D.

Example 1.1A

Hydroxylation of Oripavine to 14-hydroxymorphinone 1 kg oripavine is added with stirring to a reaction vessel containing 2.76 kg of formic acid and 0.53 kg water, and stirring is continued until the oripavine is completely dissolved, and the temperature remains in the range 20-30° C. Subsequently, 0.36 kg of 35 wt % hydrogen peroxide solution is added, and the reaction mixture is stirred for three hours or more, whilst maintaining the temperature in the range 20-35° C. The reaction vessel is cooled to 10° C. and 7.12 litres of dilute ammonium hydroxide is added slowly, whilst maintaining the reaction mixture below 40° C. If necessary, the pH of the reaction mixture is adjusted to the range 8 to 10, with more dilute ammonium hydroxide solution or hydrochloric acid as appropriate, and stirring is continued for 3-5 hours.

A precipitate of product 14-hydroxymorphinone is formed and filtered off. The precipitate is washed with water until colourless and then dried to a damp cake and collected for the next stage.

Example 1.1B

Formation of Oxymorphone Base

A hydrogenation vessel is charged with kg litre water and 0.73 kg acetic acid before adding 1 kg of 14-hydroxymorphinone prepared as in Example 1.1A and the mixture stirred until clear. 40 g of wet 10% Pd on carbon catalyst is added under a stream of nitrogen, and hydrogen supplied at 35-40 psi (2.41-2.76 bar). The temperature is maintained at 30±5° C. until hydrogen uptake stops, then the vessel is maintained at 35-40 psi (2.41-2.76 bar) and 30±5° C. for 3-4 hours. The reaction vessel is cooled to less than 25° C. and a sample subjected to HPLC to check for 14-hydroxymorphinone. If the 14-hydroxymorphinone area detected by HPLC is >0.1%, the hydrogenation is repeated.

Once it is assessed that the reaction is complete, the catalyst is filtered off, the pH of the filtrate is adjusted to pH 9 using ammonium hydroxide solution, the product precipitates and is isolated by filtration and dried under vacuum. The product is dissolved in dichloromethane/methanol (9:1 v/v) and slurried in florisil, filtered, and the filtrate is distilled to exchange to n-propanol. The n-propanol mixture is cooled and the product precipitates and is collected by filtration in 66% yield. A sample of product is tested by HPLC for alpha, beta unsaturated ketones, and is found to contain 0.51% by area measurement.

Example 1.1C

Formation of Highly Pure Oxymorphone Hydrochloride

A reaction vessel is charged with 1 kg of oxymorphone base, prepared as in Example 1.1B, together with 2.05 kg of absolute alcohol and 0.66 kg of water. The mixture is heated to 60±2° C. and stirred to form a slurry. A hydrochloric acid solution prepared from 0.66 kg concentrated hydrochloric acid, 0.24 kg of water and 0.31 kg of absolute alcohol is added to the oxymorphone base slurry and the pH checked to ensure that it is <1.0. 40 g of 10% Pd on carbon catalyst water-wet paste is added under a stream of nitrogen to the reaction mixture and the mixture is hydrogenated at 35±5 psi (2.41 bar) for 20 hours whilst maintaining a temperature of 65±3° C. The reaction mixture is filtered whilst hot through Celite and a 0.2 μm polish filter. The filtrate is cooled to 0-5° C. over 2-3 hours, and stirred for a further 2 hours to form oxymorphone hydrochloride as a precipitate. The precipitate is washed with absolute alcohol then dried. Yield is 80%.

A sample of the product is tested by HPLC for the presence of alpha, beta unsaturated ketones, and is found to contain 6.2 ppm.

Example 1.2A

Hydroxylation of Oripavine to 14-hydroxymorphinone 40 g of Oripavine is added with stirring to a reaction vessel containing 30 g of water and 85 g of formic acid, and stirring continued until oripavine is completely dissolved. The temperature remains in the range 20-30° C. Subsequently, 17.72 g of 30 wt % hydrogen peroxide solution is added, and the reaction mixture is stirred for three hours or more, whilst maintaining the temperature in the range 20-35° C. The reaction mixture is cooled to <20° C. and 335 mL of dilute ammonium hydroxide is added slowly, whilst maintaining the reaction mixture below 32° C. If necessary, the pH of the reaction mixture is adjusted to 9.0, with more dilute ammonium hydroxide solution or hydrochloric acid as appropriate, and stirring is continued for 2 hours at 20 C and 2 hours at 4-5° C.

A precipitate of 14-hydroxymorphinone is formed and filtered off. The precipitate is washed with water and then dried to a damp cake and collected for the next stage.

Example 1.2B

Formation of Oxymorphone Base

A hydrogenation vessel is charged with 148 g of water, 90.6 g of acetic acid, and 250 g of damp 14-hydroxymorphinone (48% water content), prepared as in Example 1.2A. The mixture is stirred until clear then 1.34 g of 10% Pd on carbon catalyst (dry weight) in the form of a paste is added under a stream of nitrogen. The hydrogenation vessel is flushed with nitrogen and hydrogen respectively, and then the reaction mixture is hydrogenated at 30° C. and 35 psi (2.41 bar) for 5 hours. An in process test by HPLC indicates an 14-hydroxymorphinone area of 0.07%.

Once it is assessed that the reaction is complete, the catalyst is filtered off through a pad of celite, and the celite cake is washed with 25 mL water. The filtrate is cooled to 0-5° C. and the pH is adjusted to 9.5±0.5 with 1:1 mixture (V/V) of concentrated ammonium hydroxide and water. The precipitate is stirred at 0-5° C. for one hour and isolated by filtration. The crude product is dried in vacuum oven at 50° C. to afford 113 g (86.9% yield) of light beige solid. A sample of product is tested by HPLC for alpha, beta unsaturated ketone, and is found to contain 0.27% by area measurement.

113 g of crude oxymorphone base is taken up in 1.13 L of dichloromethane/methanol (9:1, v/v). 113 g of florisil is added to the solution and the mixture is stirred for 12 hours. The mixture is filtered through a pad of 113 g of florisil, and the florisil cake is rinsed with 120 mL of dichloromethane/methanol. The solvent is removed by distillation and then switched to n-propanol. The batch is cooled to 0-5° C. and stirred for 1 hour to precipitate the oxymorphone base, which is filtered off, washed with cold n-propanol, and dried in a vacuum oven to afford 67.2 g (59.47%) of white solids.

A sample of product is tested by HPLC for alpha, beta unsaturated ketones, and is found to contain 0.027% by area measurement.

Example 1.2C

Formation of Highly Pure Oxymorphone Hydrochloride

A reaction vessel is charged with 50.1 g of oxymorphone base, prepared as in Example 1.2B, together with 120 g of absolute alcohol. The mixture is heated to 60±2° C. and stirred to form a slurry. A hydrochloric acid solution prepared from 32.7 g concentrated hydrochloric acid and 33.6 g of water is added to the oxymorphone base slurry and the pH is checked to ensure that it is <1.0. 2.0 g of 10% Pd on carbon catalyst water-wet paste is added under a stream of nitrogen to the reaction mixture and the mixture is hydrogenated at 35 psi (2.41 bar) for 20 hours whilst maintaining a temperature of 65° C. The reaction mixture is filtered whilst hot through Celite. The filtrate is cooled to 0-5° C. over 2-3 hours, and stirred for a further 2 hours to form oxymorphone hydrochloride as a precipitate. The precipitate is filtered off, washed with absolute alcohol and then dried to afford white crystals in 77% yield.

A sample of the product is tested by HPLC for the presence of alpha, beta unsaturated ketones, and is found to contain 1.1 ppm.

The above method may be varied by the skilled person whilst still maintaining excellent purity of the product oxymorphone hydrochloride, and examples of such variations follow.

Example 2.1B

Reduction of 14-hydroxymorphinone to Oxymorphone Base

A hydrogenation vessel is charged with 2.5 kg of water and 0.73 kg of acetic acid and 1 kg of 14-hydroxymorphinone is added to the vessel. The reaction mixture is stirred until a clear solution is obtained before 40 g of wet 10% Pd on carbon catalyst is added under a stream of nitrogen. Hydrogen is supplied at 35-40 psi (2.41-2.76 bar). The temperature is maintained at 30±5° C. until hydrogen uptake stops, then the vessel is maintained at 35-40 psi (2.41-2.76 bar) and 30±5° C. for 3-4 hours. The reaction vessel is cooled to less than 25° C. and a sample subjected to HPLC to check for 14-hydroxymorphinone. If the 14-hydroxymorphinone area detected by HPLC is >0.1%, the hydrogenation is repeated.

Once it is assessed that the reaction is complete, the catalyst is filtered off, dichloromethane/methanol (9:1 v/v) is added to the filtrate and the mixture is adjusted to pH 9-10 by adding ammonium hydroxide solution. The dichloromethane/methanol phase is separate, slurried in florisil, filtered, and the filtrate is distilled to exchange to n-propanol. The n-propanol mixture is cooled and the product precipitates and is collected by filtration in 73% yield. A sample of product is tested by HPLC for alpha, beta unsaturated ketones, and is found to contain 0.32% by area.

Example 2.2B

Reduction of 14-hydroxymorphinone to Oxymorphone Base

A hydrogenation vessel is charged with 35 g of water, 17 g of acetic acid and 38.08 g of 14-hydroxymorphinone, prepared in Example 1.2A. The reaction mixture is stirred until a clear solution is obtained before 1.8 g of wet 5% Pd on carbon catalyst is added under a stream of nitrogen. Hydrogen is supplied at 35-40 psi (2.41-2.76 bar). The temperature is maintained at 30±5° C. until hydrogen uptake stops, then the vessel is maintained at 35-40 psi (2.41-2.76 bar) and 30±5° C. for 4 hours. The reaction vessel is cooled to less than 25° C., and a sample is analyzed by HPLC to check for 14-hydroxymorphinone. The 14-hydroxymorphinone area detected by HPLC is 0.26%.

Once it is assessed that the reaction is complete, the catalyst is filtered off and the cake is washed with 15 mL of water. 180 mL of dichloromethane/methanol (9:1, v/v) are added to the filtrate and the pH of the mixture is adjusted to pH 9-10 by adding concentrated ammonium hydroxide. The dichloromethane/methanol layer is separated and purified by slurrying with ca. 20 g florisil. The slurry is filtered and the filtrate is distilled to exchange into n-propanol, and the mixture is cooled to 0-5° C. and stirred for 1-2 hours to precipitate oxymorphone base, which is isolated by filtration. The oxymorphone base is then slurried from n-propanol providing product in 74% yield. A sample of product is tested by HPLC for alpha, beta unsaturated ketones, and is found to contain 0.32% by area.

Example 2.2C

Formation of Highly Pure Oxymorphone Hydrochloride

A reaction vessel is charged with 2.5 g of oxymorphone base, prepared as in Example 2.2B, together with 7.5 mL of absolute alcohol, 2.5 g of water and 1.66 g of concentrated hydrochloric acid. The mixture is heated to 50-60° C. and a solution results. The pH is checked to ensure that it is <1.0. 0.111 g of 10% Pd on carbon catalyst water-wet paste is added under a stream of nitrogen to the reaction mixture and the mixture is hydrogenated at 35±5 psi (2.41 bar) for 21 hours whilst maintaining a temperature of 65±3° C. The reaction mixture is filtered whilst hot through a 0.45 μm filter. The filtrate is cooled to 0-5° C. over 2-3 hours, and stirred for a further 2 hours to form oxymorphone hydrochloride as a precipitate. The precipitate is filtered off, washed with cold absolute alcohol and dried under vacuum to afford white crystals in 77% yield.

A sample of the product is tested by HPLC for the presence of alpha, beta unsaturated ketones, and is found to contain 2.8 ppm.

Example 3.1B

Reduction of 14-hydroxymorphinone to Oxymorphone Hydrochloride

The procedure for forming the oxymorphinone free base is followed as shown above, but instead of isolating the free base from a dichloromethane/methanol solution, 0.35 volume equivalents of 3N hydrochloric acid are added (vs the volume of the dichloromethane/methanol solution), the reaction mixture is stirred, allowed to stand, and the aqueous layer (contains the product) is separated from the organic layer. The aqueous layer is distilled under vacuum to remove ca. 50% of the volume, and then the remaining solution is cooled over 2 hour to 20-25° C., stirred for 1-2 hours, cooled to 0-5° C. and stirred 2-3 hours. The white solids that form during stirring are filtered off and washed with cold isopropanol. The yield is 64% and the product contains 0.34% of alpha, beta unsaturated ketones.

Example 3.1C

Purification of Oxymorphone Hydrochloride

Using an analogous process to Example 1.1C, but starting from the product of Example 3.1B, purified oxymorphone hydrochloride is obtained in a yield of 92% and having an undetectable content of alpha, beta unsaturated ketones.

Example 3.2C

Preparation of Highly Pure Oxymorphone Hydrochloride

A reaction vessel is charged with 5.05 g of oxymorphone hydrochloride, prepared in Example 3.1B, together with 13.5 mL of absolute alcohol, 4.5 mL of water and 1.51 g of concentrated hydrochloric acid. The mixture is heated to 50-60° C. and a solution results. The pH is checked to ensure that it is <1.0. 0.21 g of 10% Pd on charcoal catalyst water-wet paste is added under a stream of nitrogen to the reaction mixture and the mixture is hydrogenated at 35±5 psi (2.41 bar) for 20 hours whilst maintaining a temperature of 65±3° C. The reaction mixture is filtered whilst hot through a 0.45 µm filter. The filtrate is cooled to 0-5° C. over 2-3 hours, and stirred for a further 2 hours to form a precipitate. The precipitate is collected by filtration, washed with cold absolute alcohol then dried. Yield is 92%.

A sample of the product is tested by HPLC and found to have an undetectable content of alpha, beta unsaturated ketones.

Without changing the basic process steps, but with small variations in the process steps for starting materials, such as isolation or not of such starting materials, and utilising the essential reduction requirements of the invention for the final step to the purified oxymorphone hydrochloride, other products have been obtained with levels of alpha, beta unsaturated ketones of 3.8 ppm, 1.7 ppm, 6.2 ppm, 6.9 ppm, 2.8 ppm, 3.1 ppm, 0.9 ppm, 6.0 ppm and another undetectable, or zero.

Example 3.2D

Hydration of Oxymorphone Hydrochloride

A drying dish is charged with oxymorphone hydrochloride, prepared as in Example 1.1C, 1.2C, 2.2C, 3.1C or 3.2C, which contains about 5-13 wt % of ethanol. The sample is placed in a vacuum oven along with a dish containing 100 mL of water. A vacuum is applied at 24-29 in Hg and the oven maintained at 20-40° C. for 24 hours. An ethanol-free or low ethanol (approx. 0.04 wt %) product is afforded containing about 10-13 wt % of water. The water absorbed by the sample may be removed in a vacuum oven at 50-55° C. The drying process is stopped when the product's KF is 6-8 wt %. The final hydrated oxymorphone hydrochloride affords a uniform polymorph with a consistent X-ray diffraction pattern.

What is claimed:

1. Oxymorphone hydrochloride having less than 10 ppm, as measured by HPLC, of 14-hydroxymorphinone.

2. Oxymorphone hydrochloride according to claim 1, wherein the content of 14-hydroxymorphinone is less than 5 ppm.

3. A pharmaceutical formulation comprising at least one pharmaceutically acceptable excipient and the oxymorphone hydrochloride according to claim 1.

4. A method of treating pain comprising administering a pharmaceutical formulation according to claim 3 to a patient in need thereof.

5. A method of purifying a starting material of either oxymorphone or oxymorphone hydrochloride to yield the oxymorphone hydrochloride according to claim 1, comprising exposing the starting material oxymorphone or oxymorphone hydrochloride to hydrogen under reducing conditions in a strongly acid water and alcohol solvent reaction medium at a temperature in the range from 60 to 70° C. for a time sufficient to provide the less than 10 ppm of 14-hydroxymorphinone.

6. The method according to claim 5, wherein the exposing is carried out for a period of at least 20 hours.

7. The method according to claim 5, wherein the reaction medium has a pH of less than 1.

8. The method according to claim 5, wherein the acid is hydrochloric acid.

9. The method according to claim 5, wherein the temperature is approximately 65° C.

10. The method according to claim 5, wherein the starting material oxymorphone or oxymorphone hydrochloride has not been isolated from a reaction mixture in which it is formed.

11. The method according to claim 5, wherein the starting material oxymorphone or oxymorphone hydrochloride has been prepared by a process comprising reduction of 14-hydroxymorphinone.

12. The method according to claim 11, wherein the 14-hydroxymorphinone that is reduced is prepared by a process of hydroxylating oripavine.

13. The method according to claim 12, wherein the oripavine is derived from concentrated poppy straw.

14. The method according to claim 13, wherein the concentrated poppy straw is derived from a high-Thebaine-yielding strain of poppy.

15. The method according to claim 5, comprising the additional steps of subsequently forming crystalline oxymorphone hydrochloride and removing residual alcohol molecules from within the crystal structure of the crystalline oxymorphone hydrochloride by exposing the crystalline oxymorphone hydrochloride to water vapour, such that the residual alcohol molecules are displaced with water molecules.

16. The method according to claim 15, comprising the additional step of removing some of the water molecules from within the crystal structure of the oxymorphone hydrochloride by exposure to reduced pressure.

17. The method according to claim 15, comprising the additional step of removing some of the water molecules from within the crystal structure of the oxymorphone hydrochloride by heating the oxymorphone hydrochloride to a temperature in the range of from 50 to 55° C. under reduced pressure.

18. A method of making hydrated oxymorphone hydrochloride having less than 10 ppm, as measured by HPLC, of 14-hydroxymorphinone and a KF of 6-8 wt %, comprising exposing a starting material of oxymorphone or oxymorphone hydrochloride to gaseous hydrogen under reducing conditions in a strongly acid water and alcohol solvent reaction medium at a temperature in the range from 60 to 70° C., subsequently forming crystalline oxymorphone hydrochloride, and removing residual alcohol molecules from within the crystal structure of the crystalline oxymorphone hydrochloride by exposing the oxymorphone hydrochloride to water vapour, such that the residual alcohol molecules are displaced with water molecules.

19. Hydrated oxymorphone hydrochloride having less than 10 ppm, as measured by HPLC, of 14-hydroxymorphinone and having peaks within the following 20 ranges when analyzed by Powder X-Ray Diffraction: 8.5-9.5, 11.0-12.0, 11.5-12.5, 12.4-13.4, 15.2-16.2, 17.6-18.6, 19.3-20.3, 19.9-20.9, 24.6-25.6, 24.9-25.9, 29.0-30.0 and 31.0-32.0.

20. Oxymorphone hydrochloride prepared by the method of claim 5.

21. Hydrated oxymorphone hydrochloride prepared by the method of claim 18.

* * * * *

UNITED STATES PATENT AND TRADEMARK OFFICE
CERTIFICATE OF CORRECTION

| | | |
|---|---|---|
| PATENT NO. | : 7,851,482 B2 | Page 1 of 1 |
| APPLICATION NO. | : 11/866840 | |
| DATED | : December 14, 2010 | |
| INVENTOR(S) | : Jen-Sen Dung et al. | |

It is certified that error appears in the above-identified patent and that said Letters Patent is hereby corrected as shown below:

At column 23, line 3, delete "20 ranges" and insert therefor --2Θ ranges--.

Signed and Sealed this
Nineteenth Day of July, 2011

David J. Kappos
*Director of the United States Patent and Trademark Office*

(12) INTER PARTES REVIEW CERTIFICATE (92nd)
United States Patent
Dung et al.

(10) Number: US 7,851,482 K1
(45) Certificate Issued: Jul. 7, 2015

(54) METHOD FOR MAKING ANALGESICS

(75) Inventors: Jen-Sen Dung; Emo M. Keskeny; James J. Mencel

(73) Assignee: DEUTSCHE BANK AG

Trial Number:

IPR2014-00160 filed Nov. 18, 2013

Petitioner: Amneal Pharmaceuticals, LLC

Patent Owner: Endo Pharmaceuticals, Inc.

Inter Partes Review Certificate for:

Patent No.: 7,851,482
Issued: Dec. 14, 2010
Appl. No.: 11/866,840
PCT Filed: Oct. 3, 2007

The results of IPR2014-00160 are reflected in this inter partes review certificate under 35 U.S.C. 318(b).

INTER PARTES REVIEW CERTIFICATE
U.S. Patent 7,851,482 K1
Trial No. IPR2014-00160
Certificate Issued Jul. 7, 2015

AS A RESULT OF THE INTER PARTES REVIEW PROCEEDING, IT HAS BEEN DETERMINED THAT:

Claim 4 is cancelled.

\* \* \* \* \*